US006926658B2

(12) United States Patent
Farnan

(10) Patent No.: US 6,926,658 B2
(45) Date of Patent: Aug. 9, 2005

(54) RADIATION DELIVERY CATHETER FOR USE WITH AN INTRALUMINAL RADIATION TREATMENT SYSTEM

(75) Inventor: Robert C. Farnan, Duluth, GA (US)

(73) Assignee: Novoste Corporation, Norcross, GA (US)

(*) Notice: Subject to any disclaimer, the term of this patent is extended or adjusted under 35 U.S.C. 154(b) by 121 days.

(21) Appl. No.: 09/775,690

(22) Filed: Feb. 1, 2001

(65) Prior Publication Data

US 2002/0161273 A1 Oct. 31, 2002

Related U.S. Application Data

(60) Provisional application No. 60/178,962, filed on Feb. 1, 2000.

(51) Int. Cl.[7] ................................................. A61N 5/00
(52) U.S. Cl. ........................................................ 600/3
(58) Field of Search ............................ 600/29–31, 37; 604/35, 43, 103.1

(56) References Cited

U.S. PATENT DOCUMENTS

| 5,135,487 A | 8/1992 | Morrill et al. |
| 5,683,345 A * | 11/1997 | Waksman et al. ............ 600/3 |
| 5,693,015 A | 12/1997 | Walker et al. |
| 5,785,685 A | 7/1998 | Kugler et al. |
| 6,203,485 B1 * | 3/2001 | Urick ............................ 600/3 |

OTHER PUBLICATIONS

International Search Report dated Apr. 18, 2001.

* cited by examiner

Primary Examiner—Samuel G. Gilbert
(74) Attorney, Agent, or Firm—Cook, Alex, McFarron, Manzo, Cummings & Mehler, Ltd.

(57) ABSTRACT

Apparatus includes an elongated flexible catheter having proximal and distal end portions, with fluidly connected coaxial lumens extending therebetween, and a diameter sufficiently small for insertion into a patient's intraluminal passageways. One or more treating elements are positionable within one of the lumens and movable between the proximal and distal portions by fluid flowing through the lumens. The distal portion includes a distal guide wire lumen having a proximal exit port distally located relative to the treatment elements positioned at the distal portion. To simultaneously achieve stiffness along the proximal portion and flexibility along the distal portion, the inner and/or outer coaxial members may be of more than one-piece construction. The inner and/or outer members may also be stepped or bumped in diameter to decrease the pressure and fluid transit times within the catheter. A balloon may be added to the distal portion for positioning the catheter or performing angioplasty.

6 Claims, 1 Drawing Sheet

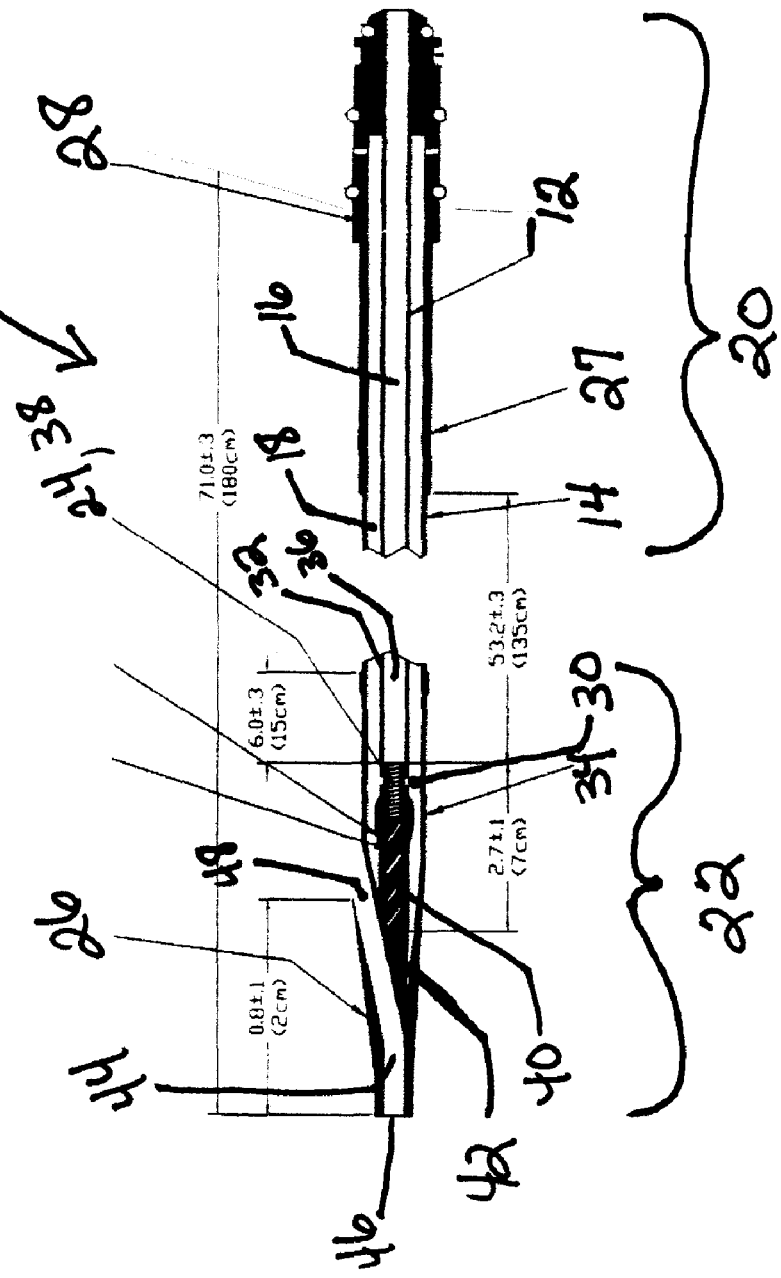

RADIATION DELIVERY CATHETER FOR USE WITH AN INTRALUMINAL RADIATION TREATMENT SYSTEM

CROSS-REFERENCE TO RELATED PATENTS AND APPLICATIONS

This application claims the benefit of U.S. Provisional Application Ser. No. 60/178,962, filed Feb. 1, 2000. The disclosures of U.S. Pat. No. 5,683,345, issued Nov. 4, 1997; U.S. Pat. No. 5,899,882 issued May 4, 1999; U.S. Pat. No. 6,013,020 issued Jan. 11, 2000; U.S. patent applications Ser. Nos. 09/304,752, filed May 4, 1999; 09/679,950, filed Oct. 4, 2000; and U.S. provisional application serial No. 60/143,730, filed Jul. 14, 1999, are incorporated herein by reference.

FIELD OF THE INVENTION

The present invention relates generally to the delivery of treating elements by a catheter to a selected location within the intraluminal passageways of a patient. Intraluminal passageways are defined herein as all lumens, passageways, conduits, ducts, channels, canals, vessels, and cavities within the human body. More particularly, the present invention relates to the apparatus for delivery of a treating element, such as a radioactive source, through a catheter to a desired site, such as a coronary artery, for inhibiting wound healing response, such as restenosis following a balloon angioplasty, and also for inhibiting other occurrences of cell migration, proliferation, and enlargement, including that of cancerous cells, which may not result from wound healing response.

BACKGROUND OF THE INVENTION

The present invention consists of a radiation delivery catheter that is compatible with the transfer device described in the above-identified patents and patent applications that are referenced herein. The radiation delivery catheter is a component of a system designed to reduce the frequency of restenosis (re-blockage) in coronary arteries after balloon angioplasty or other interventional procedure. The catheter is inserted into the patient using a guide wire and guide catheter previously positioned in the patient for the balloon angioplasty procedure; the catheter is then connected to the transfer device and the distal tip of the catheter is guided to the treatment site in the artery. Radioactive treatment elements are hydraulically or pneumatically delivered from the transfer device to the treatment site, and after the appropriate dosage has been delivered, the sources are returned into the transfer device by reversing direction of the fluid flow.

BRIEF DESCRIPTION OF DRAWINGS

FIG. 1 is a cross-sectional view of the elongated catheter tube of the present invention.

DETAILED DESCRIPTION OF INVENTION

As seen in FIG. 1, the catheter 10 of the present invention consists of coaxial inner and outer tubular members 12 and 14, each having a lumen extending along a major portion of the catheter's length. The inner tubular member 12 contains the radiation source lumen 16 for transitioning the radioactive treatment elements in and out of the catheter 10. The outer tubular member 14 contains the fluid return lumen 18 for fluid bypass and for retrieving the radioactive treatment elements. This coaxial design centers the radioactive elements within the catheter 10, which may be helpful in reducing "hot spots" along the tissue being treated. Also, having the inner member 12 centered within an outer member 14 protects the source lumen 16 from buckling or kinking under the force created when tightening a hemostasis valve that is commonly used for preventing blood backflow through the guiding catheter.

To facilitate passage of the catheter 10 through a guiding catheter, over a guide wire and across the treatment site and to prevent kinking of the source lumen 16 when manipulated through tortuous anatomy, the proximal segment 20 of the catheter 10 shall have sufficient column strength and the distal segment 22 of the catheter 10 shall have sufficient flexibility. At the very minimum, the catheter 10 shall be capable of attaining a bend radius of 0.25 inch without kinking and obstructing the source lumen passageway 16. Preferably, the catheter 10 would be able to maintain a 0.5 inch bend radius while allowing the sources to easily transit to and from said distal portion 22 of catheter 10. The catheter's column strength and flexibility shall be such that the catheter 10 can be guided to distal treatment sites within vessels of 2.0 to 2.5 mm minimum reference diameter.

In conjunction with the flexibility and stiffness of the catheter 10, the overall outside diameter of the catheter 10 will determine how far the catheter 10 can successfully be advanced into the vasculature. Obviously, a smaller catheter can navigate smaller, more distal vessels. However, certain constraints, such as the size and the desired transit time of the radioactive treatment elements, and maximum pressure within the catheter, determine the effective catheter diameter. Considering all the constraints, the catheter 10 will most likely have an outer diameter in the range of 3.0 to 4.5 French. For a maximum catheter pressure of 120 psi and a desired transit time of no more than 5 seconds, the catheter 10 outside diameter will be approximately 3.5 French.

The catheter 10 of the present invention consists of an inner tubular member 12, an outer tubular member 14, a radiopaque spring marker 24, a radiopaque distal tip 26, strain relief tubing 27 and a proprietary connector 28.

The inner and outer coaxial members 12 and 14 are elongated tubes, each having a lumen there through. The inner coaxial member 12 resides within the outer coaxial member 14 and has one or more openings 30 at its distal end 32 for providing fluid communication between the inner lumen 16 and the outer lumen 18. The inner coaxial member 12 may be made of nylon, PEBAX (polyetherblock amides), polyimide or other suitable materials for producing the needed catheter stiffness and flexibility. The outer coaxial member 14 may be made of nylon, polyimide or other suitable materials. Additionally, the interior wall of the inner member 12 may be lined with Teflon (PTFE or polytetraflouroethylene) to reduce the coefficient of friction for faster transit times of the radioactive treatment elements. To simultaneously achieve the needed stiffness along the proximal and intermediate segments 20 and 21 of the catheter 10 and the needed flexibility at the distal segment 22 of the catheter 10, the inner and/or outer coaxial members 12 and 14 may be of two piece construction. Therefore, different materials can be used at both ends to achieve the desired stiffness and flexibility. A two piece inner member comprises an inner member 12 and a distal inner member 32, and a two piece outer member comprises an outer member 14 and a distal outer member 34. The inner and outer members 12 and 14 may be made of polyimide for stiffness and the distal inner and distal outer members 32 and 34 may be made of PEBAX and nylon respectively to create a soft distal catheter segment 22. Other materials such as FEP may be sandwiched between layers of polyimide for tubing construction purposes. To enhance the bonding performance of the distal inner member 32 to the inner member 12 and the distal outer member 34 to the outer member 14, the exterior of the inner member 12 may be coated with urethane or other similar materials.

The radiopaque spring marker 24 resides within the distal end 22 of the inner member lumen 16, or in the case of a two piece construction, within the distal inner member lumen 36. The spring marker 24 is made up of radiopaque materials, such as stainless steel, platinum, platinum-iridium or gold, that will provide clear visualization under fluoroscopic imagery. The main purposes for having the distally placed internal marker 24 are to provide a stop for the treatment elements as they travel to the distal end 22 of the catheter 10 and to indicate to the user the distal most point of the radioactive treatment elements when placed for treatment. This spring marker 24 is substituted for the intraluminal connector set forth in the patents and applications referenced herein. Unlike a rigid marker, the spring marker 24 flexes as the distal segment 22 of the catheter 10 travels around bends, making it easier to advance the catheter 10 through tortuous anatomy. The spring 24 is preferably of variable pitch. The proximal portion 38 of the spring 24 has a closed pitch so as to reinforce the inner member 12 and prevent it from kinking or collapsing. The closed pitch portion 38 is adjacent to the one or more openings 30 within the inner member wall and allows fluid flow through the coils for fluid communication between the inner and outer members 12 and 14. The distal portion 40 of the spring 24 has an open pitch to distance the rest of the spring 24 and fluid communication openings 30 away from the soft plug or adhesive 42 that will be used to fuse the inner and outer members together 12 and 14.

A radiopaque tip 26 having a single operator exchange guide wire lumen 44 is fused to the distal ends of the inner and outer members 12 and 14. The distal guide wire lumen 44 has an opening 46 at its distal tip and has a proximal exit port 48 that is distal to the radioactive treatment elements. Preferably, the length of the guide wire lumen 44 is 5 cm or less; although, it shall be of sufficient length to facilitate placement of the catheter 10 across the treatment site. The distal guide wire lumen 44 shall pass a standard guide wire without significant resistance. The tip 26 shall be soft and flexible to minimize risk of vessel damage during use. Tungsten loaded PEBAX may be used to create a soft distal tip 26 that is radiopaque. PEBAX or other soft material may be layered over the tungsten loaded PEBAX.

The radiation delivery catheter 10 interfaces with a transfer device through a proprietary connector 28 as described in the above referenced patents and applications. The proprietary connector 28 is attached to the proximal end of the catheter and allows the sources to transition freely from the transfer device to the catheter and vice versa. The two piece construction of the proprietary connector 28 includes an external component having a lumen along its entire length and an internal component, referred to as the puck, residing therein. The proximal end of the outer tubular member 14 is positioned between the inner wall of the exterior component and the external wall of the puck. The proximal end of the inner tubular member 12 extends through a central lumen through the puck.

To improve the hydraulic efficiency of the above described catheter 10, the inner and or outer tubular members 12 and 14 may be stepped or "bumped" in diameter to decrease the pressure and fluid transit times within the catheter 10. If the inner tubular member 12 is bumped, the wall thickness of the inner member 12 increases at the distal segment 22, causing the inner diameter of the outer member 14 to decrease at the distal end 22. The inner diameter of the inner member 12 and the outer diameter of the outer member 14 stay constant, while the inner diameter of the outer member 14 steps down to a smaller diameter along the distal segment 22. If the outer tubular member 14 is bumped, the outer and inner diameters of the outer member 14 step down to a smaller diameter, while the inner and outer diameters of the inner tubular 12 member remain constant. If both the inner and outer tubular members 12 and 14 are bumped, the distal segment 22 of the inner member 12 has an increased wall thickness in addition to the distal segment 22 of the outer member 14 being stepped down to smaller internal and external diameters.

Any of the above described embodiments of the present invention may also include an angioplasty or centering balloon attached to the distal portion 22 of the outer tubular member 14. The balloon is in fluid communication with the fluid return lumen 18 (outer member lumen) so that the balloon expands as the fluid flows through the catheter 10. Most likely to deflate the balloon, suction will be applied to the outer member lumen 18.

Any of the catheter embodiments of the present invention may be used with the injury sizing tool described in U.S. patent application Ser. No. 09/679,950, which is referenced herein.

What is claimed is:

1. A catheter for delivering treatment elements to a selected site within the intraluminal passageways of a body, the catheter comprising:

elongated inner and outer tubular members, said inner member having a first lumen therein and positioned coaxially within said outer member having a second lumen therein and each said members having a proximal segment and a distal segment, said first and second lumens being in fluid-tight communication with each other at said distal segments of said tubular members;

a radiopaque spring residing within said distal segment of said inner member;

a distal tip formed at the distal segments of said inner and outer tubular members, said distal tip having a first opening and a second opening, said second opening proximal to said first opening, and a third lumen for receiving a guide wire extending between said openings.

2. The catheter of claim 1 further comprising an outside diameter of approximately 3.5 French.

3. The catheter of claim 1 wherein said radiopaque spring member consists of stainless steel, platinum, platinum-iridium or gold.

4. The catheter of claim 1 wherein said radiopaque spring member consists of stainless steel, platinum, platinum-iridium or gold.

5. A catheter for delivering treatment elements to a selected site within the intraluminal passageways of a body, the catheter comprising:

elongated inner and outer tubular members, said inner member having a first lumen and positioned coaxially within said outer member having a second lumen therein and each said members having a proximal segment and a distal segment, said first and second lumens being in fluid-tight communication with each other at said distal segments of said tubular members; and a radiopaque spring member residing within said distal segment of said first lumen.

6. The catheter of claim 5 further comprising an outside diameter of approximately 3.5 French.

* * * * *